US010702225B2

United States Patent
Nam et al.

(10) Patent No.: US 10,702,225 B2
(45) Date of Patent: Jul. 7, 2020

(54) MOBILE X-RAY IMAGING APPARATUS

(71) Applicant: Samsung Electronics Co., Ltd., Suwon-si, Gyeonggi-do (KR)

(72) Inventors: Jae Won Nam, Yongin-si (KR); Ku Il Jang, Yongin-si (KR); Chang Jin Yang, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 16/283,586

(22) Filed: Feb. 22, 2019

(65) Prior Publication Data
US 2019/0183440 A1 Jun. 20, 2019

Related U.S. Application Data

(63) Continuation of application No. 15/317,401, filed as application No. PCT/KR2016/010756 on Sep. 26, 2016, now Pat. No. 10,265,034.

(51) Int. Cl.
*A61B 6/10* (2006.01)
*A61B 6/00* (2006.01)

(52) U.S. Cl.
CPC .............. *A61B 6/10* (2013.01); *A61B 6/00* (2013.01); *A61B 6/4405* (2013.01); *A61B 6/56* (2013.01); *A61B 6/4266* (2013.01); *A61B 6/4283* (2013.01)

(58) Field of Classification Search
CPC ........... A61B 6/10; A61B 6/00; A61B 6/4405; A61B 6/56; A61B 6/4266; A61B 6/4283
See application file for complete search history.

(56) References Cited

U.S. PATENT DOCUMENTS

2012/0045037 A1* 2/2012 Carmichael .......... A61B 6/4266
378/198

OTHER PUBLICATIONS

Office Action in connection with European Application No. 16875889.4 dated Nov. 29, 2019, 4 pages.

* cited by examiner

*Primary Examiner* — Courtney D Thomas

(57) ABSTRACT

Disclosed herein is a mobile x-ray imaging apparatus having an improved structure to reinforce security of an x-ray detector. A mobile x-ray imaging apparatus includes an x-ray source configured to generate and radiate x-rays, one or more x-ray detectors provided to detect the x-rays radiated from the x-ray source, a storage unit having one or more slots in which the one or more x-ray detectors are stored, and one or more locking units installed in the storage unit to limit withdrawal of the one or more x-ray detectors stored in the one or more slots, wherein the one or more locking units may include a pressing member provided to be pressable and one or more rotating members configured to directly receive a pressing force of the pressing member and provided to rotate and protrude toward an inside of the one or more slots.

11 Claims, 15 Drawing Sheets

MOBILE X-RAY IMAGING APPARATUS

CROSS-REFERENCE TO RELATED APPLICATIONS

This application is a continuation of Ser. No. 15/317,401, which is the National Stage of International Application No. PCT/KR2016/010756, filed Sep. 26, 2016, which claims priority to Korean Patent Application No. 10-2015-0180778, filed Dec. 17, 2015, the disclosures of which are herein incorporated by reference in their entirety.

BACKGROUND

1. Field

The present disclosure relates to a mobile x-ray imaging apparatus, and more particularly, to a mobile x-ray imaging apparatus having an improved structure to reinforce security of an x-ray detector.

2. Description of Related Art

An x-ray imaging apparatus is an apparatus using x-rays to obtain an image of an inside of an object. An x-ray imaging apparatus may irradiate an object with x-rays and detect x-rays that have passed through the object to form an image of an inside of the object with a non-invasive method. A medical x-ray imaging apparatus may be used in diagnosing an injury, a disease, or the like that cannot be diagnosed from outside.

A typical x-ray imaging apparatus has an x-ray source and an x-ray detector fixed at a predetermined space. Consequently, a patient has to move to an examination room in which an x-ray imaging apparatus is disposed to perform x-ray imaging.

However, because it is difficult to perform x-ray imaging using a typical x-ray imaging apparatus in a case of a patient having mobility difficulties, a mobile x-ray imaging apparatus capable of performing x-ray imaging regardless of location has been developed.

Because a mobile x-ray imaging apparatus has an x-ray source mounted at a movable main body and uses a portable x-ray detector, x-ray imaging may be performed by directly going to a patient having mobility difficulties.

One or more x-ray detectors may be stored in a mobile x-ray imaging apparatus. Due to a characteristic of a mobile x-ray imaging apparatus being usable in various locations, there are concerns regarding a theft or security problem. Particularly, the one or more x-ray detectors are more vulnerable to a theft or security problem due to being portable.

SUMMARY

It is an aspect of the present disclosure is to provide a mobile x-ray imaging apparatus having an improved structure to prevent theft of an x-ray detector and reinforce security.

It is another aspect of the present disclosure to provide a mobile x-ray imaging apparatus having an improved structure to enable one or more x-ray detectors to be separately locked.

It is still another aspect of the present disclosure to provide a mobile x-ray imaging apparatus having an improved structure to enable one or more x-ray detectors to be simultaneously locked.

A mobile x-ray imaging apparatus according to a spirit of the present disclosure includes an x-ray source configured to generate and radiate x-rays, one or more x-ray detectors provided to detect the x-rays radiated from the x-ray source, a storage unit having one or more slots in which the one or more x-ray detectors are stored, and one or more locking units installed in the storage unit to limit withdrawal of the one or more x-ray detectors stored in the one or more slots, wherein the one or more locking units may include a pressing member provided to be pressable and one or more rotating members configured to directly receive a pressing force of the pressing member and provided to rotate and protrude toward an inside of the one or more slots.

The pressing member may vertically move in a first direction, and the one or more rotating members may rotate about a rotation shaft extending in a second direction.

The one or more locking units may further include a rotation limiting unit configured to limit rotation of the one or more rotating members, and the rotation limiting unit may face the pressing member and the one or more rotating members are placed therebetween.

The rotation limiting unit may include a rod configured to vertically move in the first direction, which is the same as a moving direction of the pressing member, and a solenoid coupled to the rod to adjust movement of the rod according to an electrical signal.

Each of the one or more rotating members may include a rod-corresponding surface configured to face the rod, and one end portion of the rod facing the rod-corresponding surface may move along the rod-corresponding surface when the one or more rotating members rotate.

A locking groove configured to limit rotation of the one or more rotating members by the one end portion of the rod being inserted thereinto may be formed to be recessed at the rod-corresponding surface.

The rod-corresponding surface may include a first portion disposed in front of a second portion in a direction in which the one or more rotating members rotate by being pressed by the pressing member and the second portion disposed behind the first portion in the direction in which the one or more rotating members rotate by being pressed by the pressing member, and formed above the first portion in the first direction.

A locking groove configured to limit rotation of the one or more rotating members by the one end portion of the rod being inserted thereinto may be formed to be recessed at the second portion.

The rod-corresponding surface may further include a third portion configured to connect the first portion to the second portion and be tilted toward the second portion in the first direction.

The rotation limiting unit may further include a casing configured to have the rod and the solenoid mounted therein and have a rod guide formed at one sidewall thereof, and a stopper that is formed to protrude from the rod may be configured to move vertically in the first direction and be coupled to the rod guide to limit vertical movement of the rod.

The pressing member may move along a guide pin coupled to the pressing member to guide movement of the pressing member, and a first elastic member configured to be repeatedly contracted and relaxed according to movement of the pressing member may be provided at the guide pin.

The one or more rotating members may rotate about a rotation shaft configured to pass through the one or more rotating members, and a second elastic member configured to be repeatedly contracted and relaxed according to rotation of the one or more rotating members may be provided at the rotation shaft.

The one or more locking units may further include a connecting member configured to connect the pressing member to the rotation limiting unit and have a guide pin through-hole through which the guide pin passes formed therein.

The one or more locking units may further include a support member installed at a partition configured to divide the one or more slots, and the rotation shaft may pass through the support member and the one or more rotating members.

The second elastic member may include a torsion spring, one end portion of the second elastic member may be fixed to one sidewall of the support member, and the other end portion of the second elastic member may be fixed to a protrusion formed at one surface of each of the one or more rotating members facing the one sidewall of the support member to which the one end portion of the second elastic member is fixed.

A mobile x-ray imaging apparatus according to a spirit of the present disclosure includes a main body, an x-ray source configured to generate and radiate x-rays, one or more x-ray detectors provided to detect the x-rays radiated from the x-ray source, a storage unit provided in the main body and having one or more slots in which the one or more x-ray detectors are stored, and one or more locking units installed in the storage unit to limit withdrawal of the one or more x-ray detectors stored in the one or more slots, wherein the one or more locking units may include a pressing member provided to be pressable and configured to vertically move in a first direction, one or more rotating members provided to rotate about a rotation shaft extending in a second direction and protrude toward the one or more slots, and a rotation limiting unit including a rod vertically moving in the first direction to limit rotation of the one or more rotating members.

A pressing force of the pressing member may be directly transmitted to the one or more rotating members.

Each of the one or more rotating members may include a rod-corresponding surface configured to face the rod, and a locking groove configured to limit rotation of the one or more rotating members by one end portion of the rod facing the rod-corresponding surface being inserted thereinto may be formed to be recessed at the rod-corresponding surface.

The rotation shaft may pass through the one or more rotating members in the second direction, and, when the pressing member is pressed, the rotation shaft may be placed above the locking groove in the first direction by rotation of the one or more rotating members.

The rod-corresponding surface may include a first portion disposed in front of a second portion in a direction in which the one or more rotating members rotate by being pressed by the pressing member and the second portion disposed behind the first portion in the direction in which the one or more rotating members rotate by being pressed by the pressing member, formed above the first portion in the first direction, and having the locking groove formed to be recessed therein.

The rod-corresponding surface may further include a third portion configured to connect the first portion to the second portion and be tilted toward the second portion in the first direction.

A slope may be formed rearward in the direction in which the one or more rotating members rotate with respect to the first direction at the one surface of the rod facing the rod-corresponding surface.

The pressing member may move along a guide pin coupled to the pressing member to guide movement of the pressing member, and a first elastic member configured to be repeatedly contracted and relaxed according to movement of the pressing member may be provided at the guide pin.

The one or more rotating members may rotate about the rotation shaft configured to pass through the one or more rotating members, and a second elastic member configured to be repeatedly contracted and relaxed according to rotation of the one or more rotating members may be provided at the rotation shaft.

The second elastic member may include a torsion spring.

A third elastic member configured to be repeatedly contracted and relaxed in the first direction according to movement of the rod may be provided at the rod. The third elastic member may be relaxed when the first elastic member is contracted, and the third elastic member may be contracted when the first elastic member is relaxed.

The one or more rotating members may rotate and protrude toward an inside of the one or more slots when a pressing force is transmitted from the pressing member.

A mobile x-ray imaging apparatus according to a spirit of the present disclosure includes an x-ray source configured to generate and radiate x-rays, a plurality of x-ray detectors provided to detect the x-rays radiated from the x-ray source, a storage unit having a plurality of slots in which the plurality of x-ray detectors are stored, and a locking unit installed at the storage unit to simultaneously limit withdrawal of the plurality of x-ray detectors stored in the plurality of slots.

The plurality of slots may include a first slot and a second slot configured to abut the first slot, and a partition is placed therebetween, and the locking unit may be installed at the partition to simultaneously limit withdrawal of the plurality of x-ray detectors stored in the first slot and the second slot.

The plurality of slots may include a first slot and a second slot that are adjacent to each other, and the locking unit may include a pressing member provided to be pressable and a plurality of rotating members including a first rotating member provided to rotate and protrude toward an inside of the first slot and a second rotating member provided to rotate and protrude toward an inside of the second slot.

A pressing force of the pressing member may be directly transmitted to the plurality of rotating members.

The pressing member may simultaneously press the plurality of rotating members.

The locking unit may further include a rotation limiting unit including a rod configured to linearly move to simultaneously limit rotation of the plurality of rotating members.

Since one or more locking units are installed in a storage unit to limit withdrawal of one or more x-ray detectors stored in one or more slots, theft of the one or more x-ray detectors can be prevented while reinforcing security at the same time.

Since a plurality of locking units are installed in the storage unit, withdrawal of a plurality of x-ray detectors stored in a plurality of slots can be separately limited.

Since a single pressing member and a single rotation limiting unit are used to simultaneously adjust rotation of a plurality of rotating members, withdrawal of the plurality of x-ray detectors stored in the plurality of slots adjacent to each other can be separately limited.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Hereinafter, an exemplary embodiment according to the present disclosure will be described in detail with reference to the accompanying drawings. Meanwhile, terms, such as "front end," "rear end," "upper portion," "lower portion," "upper end," and "lower end," that are used in the description below are defined on the basis of the drawings, and a shape and a position of each element is not limited by the terms.

Figure 1:
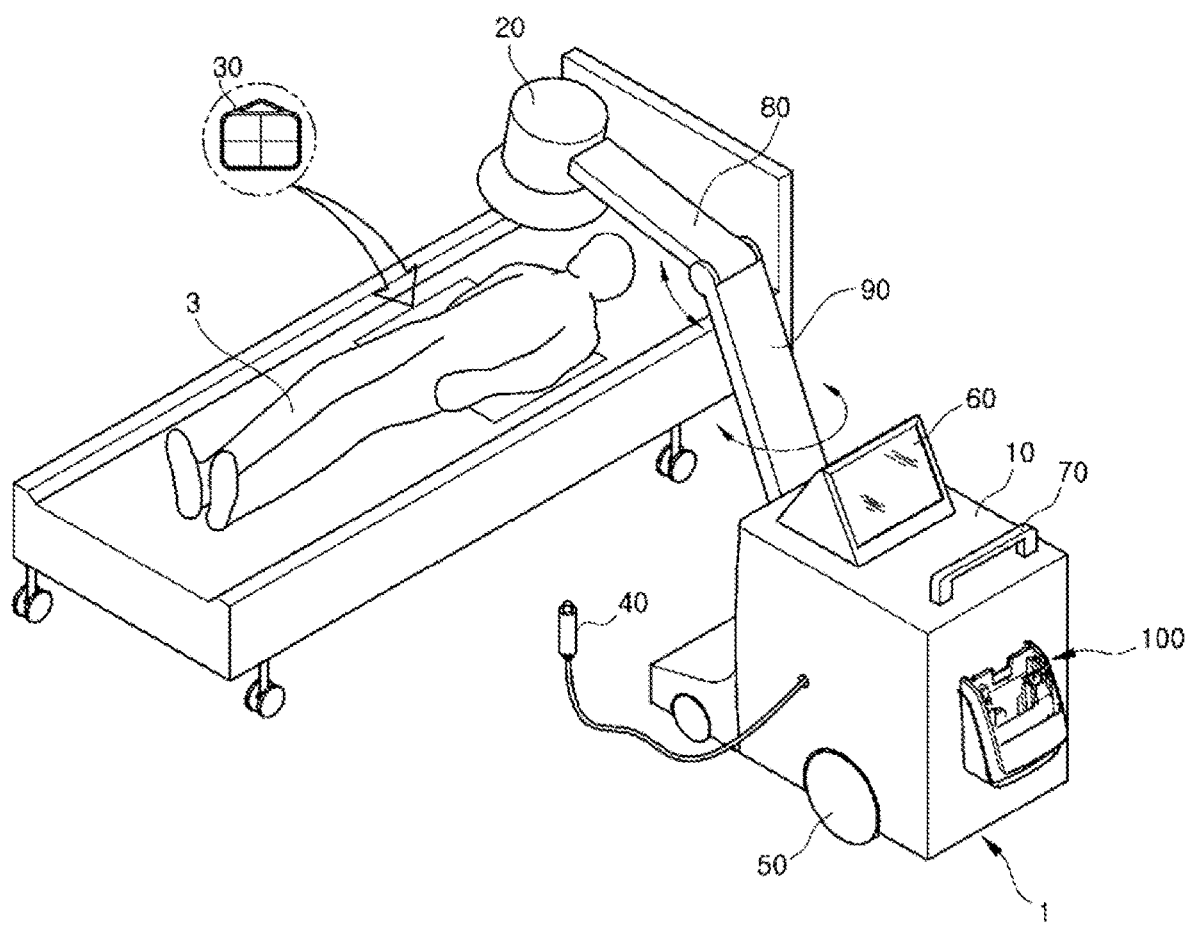
FIG. 1 is a view illustrating a usage example of a mobile x-ray imaging apparatus according to an embodiment of the present disclosure.

FIG. 1 is a view illustrating a usage example of a mobile x-ray imaging apparatus according to an embodiment of the present disclosure. Hereinafter, reference numeral "3" refers to an object to be x-rayed. Here, the object may be a living body of a human being or an animal, but is not limited thereto. The object may be anything that may have an image of an inner structure thereof formed by a mobile x-ray imaging apparatus 1.

As illustrated in FIG. 1, the mobile x-ray imaging apparatus 1 may include a main body 10. The main body 10 may be movable. A controller (not illustrated) may be provided in the main body 10. The controller may control an x-ray source 20 to control generation of x-rays. Also, the controller may receive an electrical signal from one or more x-ray detectors 30 and generate an x-ray image.

The mobile x-ray imaging apparatus 1 may further include a hand switch 40. The hand switch 40 may receive a command from a user and transmit the command to the controller. A command received by the hand switch 40 may include an x-ray radiation readying command or an x-ray radiating command. For example, a user may input the x-ray irradiation readying command through the hand switch 40 for capturing by the mobile x-ray imaging apparatus 1. Also, when preparation for capturing is finished, the user may input the x-ray radiating command through the hand switch 40 so that the x-ray source 20 radiates x-rays.

The mobile x-ray imaging apparatus 1 may further include a plurality of wheels 50 configured to give mobility to the main body 10.

The mobile x-ray imaging apparatus 1 may further include a display 60. The display 60 may display information on a patient, an x-ray image, and the like. The display 60 may be installed at the main body 10. The display 60 may include a touch screen function.

The mobile x-ray imaging apparatus 1 may further include a handle 70 provided at the main body 10. A user may grip the handle 70 and push or pull the main body 10.

The mobile x-ray imaging apparatus 1 may further include a support arm 80 and a support frame 90. The x-ray source 20 that will be described below may be mounted on the movable main body 10 by the support arm 80. The support arm 80 may be mounted on the support frame 90 to be rotatable in a vertical direction. The support frame 90 may be mounted at one side of the main body 10 to be rotatable in a horizontal direction. As a result, since the support arm 80 is rotatable and a tilt angle thereof may be changed, the x-ray source 20 may freely move.

The mobile x-ray imaging apparatus 1 may further include the x-ray source 20 configured to generate and radiate x-rays. As described above, the x-ray source 20 may be coupled to the support arm 80. The x-ray source 20 receives power and generates x-rays. Energy of x-rays may be controlled by a tube voltage, and intensity and dose of x-rays may be controlled by a tube current and x-ray exposure time.

The mobile x-ray imaging apparatus 1 may further include the one or more x-ray detectors 30 provided to detect x-rays radiated from the x-ray source 20. The one or more x-ray detectors 30 may have various sizes depending on an object of x-ray image capturing. The one or more x-ray detectors 30 may be wirelessly realized for convenience of use. The one or more x-ray detectors 30 may be stored in a storage unit 100 after capturing an x-ray image. Also, the one or more x-ray detectors 30 may be charged while being stored in the storage unit 100.

The mobile x-ray imaging apparatus 1 may further include the storage unit 100 configured to store the one or more x-ray detectors 30. The storage unit 100 may be provided at the main body 10. The storage unit 100 will be described in detail below.

The mobile x-ray imaging apparatus 1 may further include one or more locking units 200 configured to limit withdrawal of the one or more x-ray detectors 30 stored in the storage unit 100. The one or more locking units 200 will be described in detail below.

Figure 2:
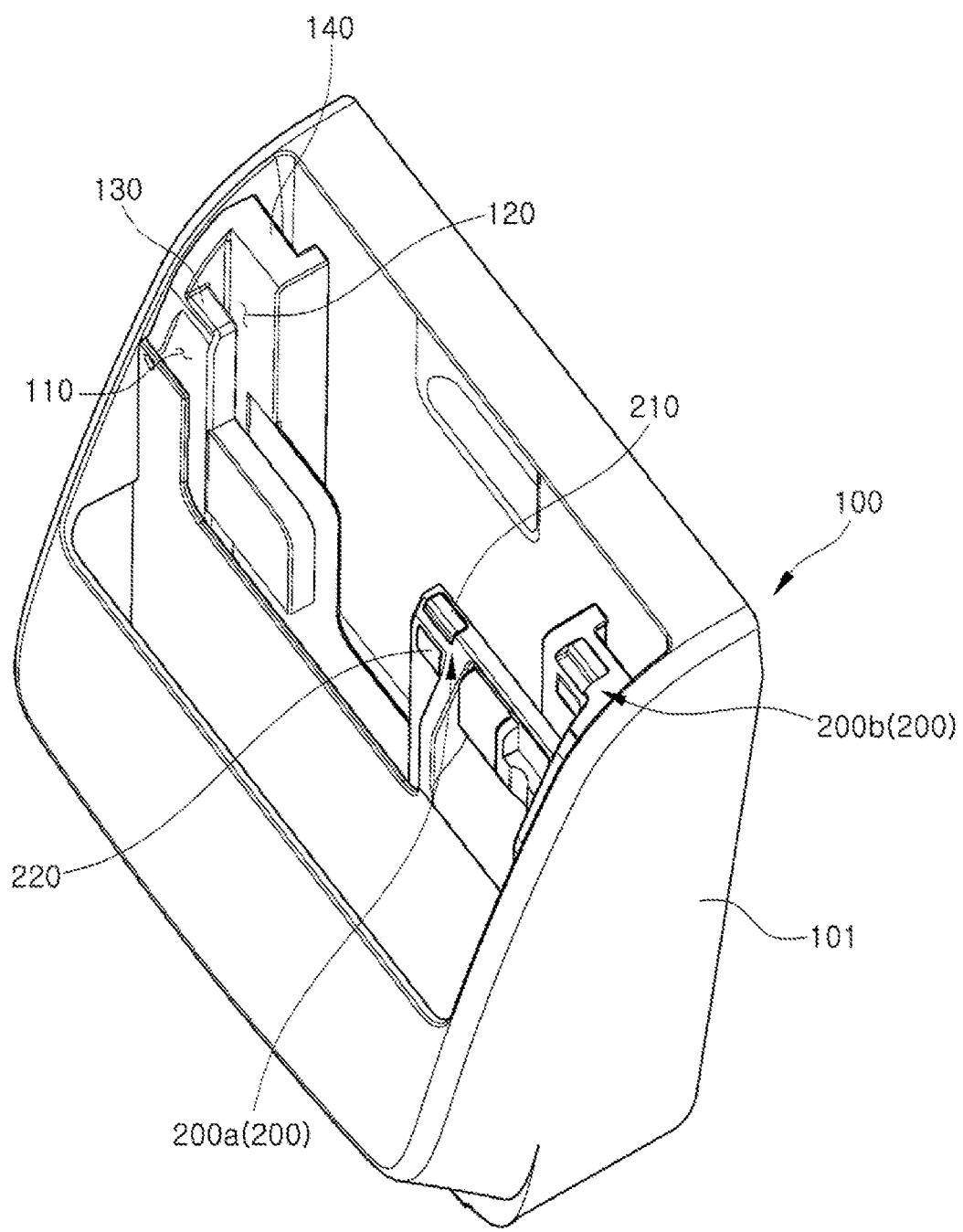
FIG. 2 is a perspective view illustrating a storage unit of the mobile x-ray imaging apparatus according to an embodiment of the present disclosure.
Figure 3:
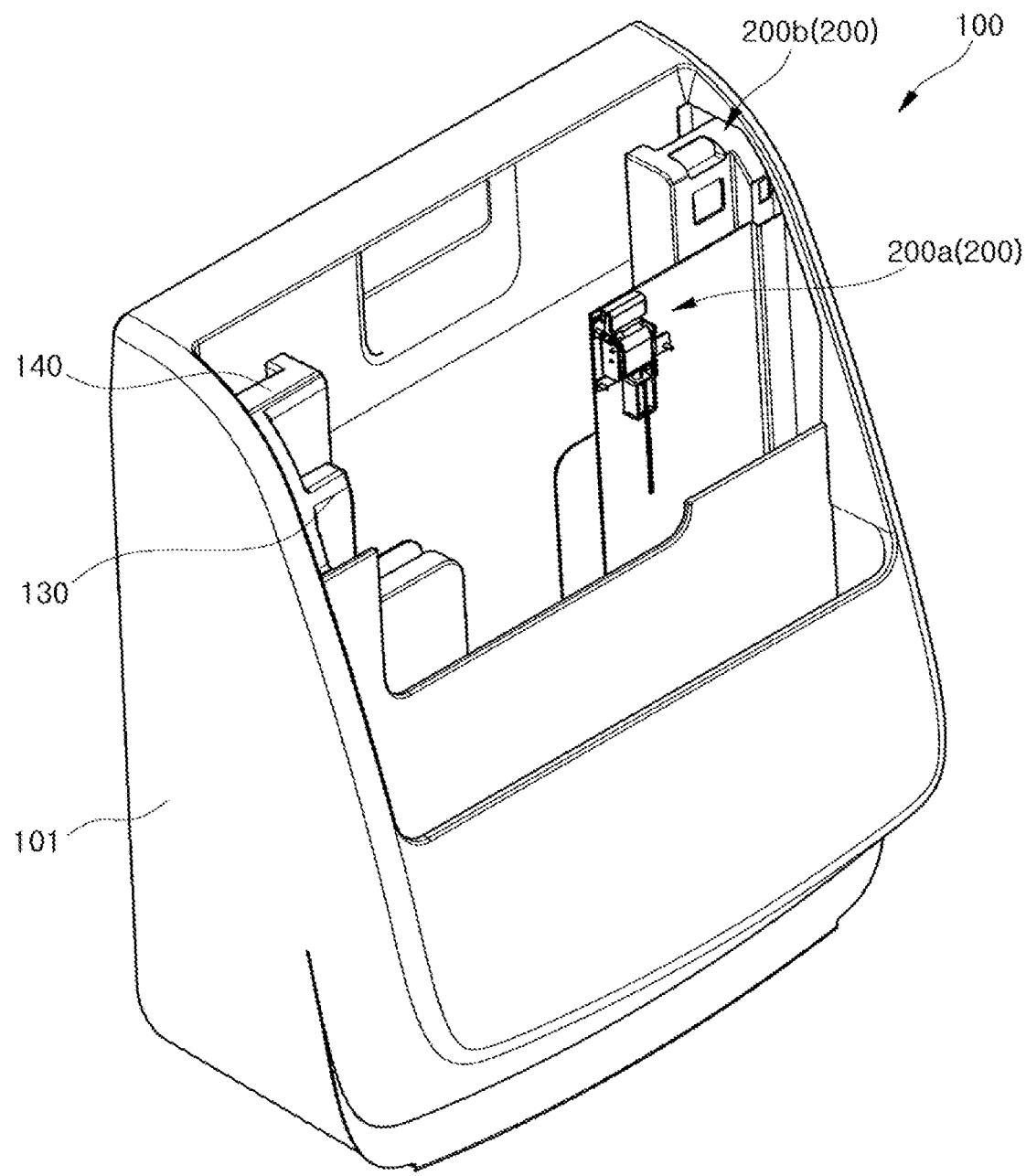
FIG. 3 is a perspective view illustrating the storage unit at a different angle from FIG. 2 so that an arrangement structure of a locking unit in the mobile x-ray imaging apparatus according to an embodiment of the present disclosure is visible.

FIG. 2 is a perspective view illustrating a storage unit of the mobile x-ray imaging apparatus according to an embodiment of the present disclosure, and FIG. 3 is a perspective view illustrating the storage unit at a different angle from FIG. 2 so that an arrangement structure of a locking unit in the mobile x-ray imaging apparatus according to an embodiment of the present disclosure is visible. In FIG. 3, some configurations of a partition 130 are omitted so that an arrangement structure of the one or more locking units 200 is seen well.

As illustrated in FIGS. 2 and 3, the storage unit 100 may include one or more slots 110 and 120 in which the one or more x-ray detectors 30 are stored.

Sizes of the one or more slots 110 and 120 may be different from each other. The sizes of the one or more slots 110 and 120 are determined according to sizes of the one or more x-ray detectors 30 stored in the one or more slots 110 and 120. For example, the one or more slots 110 and 120 may include a first slot 110 configured to store an x-ray detector having a relatively small size and a second slot 120 configured to store an x-ray detector having a relatively large size.

The first slot 110 and the second slot 120 may abut each other and the partition 130 is placed there between. The partition 130 may be formed to extend from a sidewall of a storage unit body 101 configured to form an exterior of the storage unit 100 toward an inside of the storage unit 100. The second slot 120 may be defined by the partition 130 and a frame 140. The frame 140 may be formed to extend from the sidewall of the storage unit body 101 toward the inside of the storage unit 100 to be spaced a predetermined distance apart from the partition 130. The frame 140 and the partition 130 may be parallel to each other.

Sizes of the one or more slots 110 and 120 are not limited to being different from each other and may be modified in various ways. For example, sizes of the one or more slots 110 and 120 may be the same. Also, the number of the one or more slots 110 and 120 is not limited to two. However, a case in which the one or more slots 110 and 120 include the first slot 110 and the second slot 120 will be mainly described as an example.

The mobile x-ray imaging apparatus 1 may further include the one or more locking units 200 installed in the storage unit 100 to limit withdrawal of the one or more x-ray detectors 30 stored in the one or more slots 110 and 120.

The one or more locking units 200 may separately limit withdrawal of the one or more x-ray detectors 30 stored in the one or more slots 110 and 120. Specifically, the one or more locking units 200 may include a first locking unit 200a configured to limit withdrawal of an x-ray detector stored in the first slot 110 and a second locking unit 200b configured to limit withdrawal of an x-ray detector stored in the second slot 120.

The one or more locking units 200 may be installed in the storage unit 100. For example, the first locking unit 200a may be installed in the partition 130. Specifically, the first locking unit 200a may be installed in the partition 130 so that a portion thereof is exposed to the outside. The second locking unit 200b may be installed in the frame 140. Specifically, the second locking unit 200b may be installed in the frame 140 so that a portion thereof is exposed to the outside. When described according to another aspect, the one or more locking units 200 may be installed in the storage unit 100 to be adjacent to inlets of the one or more slots 110 and 120.

Figure 4:
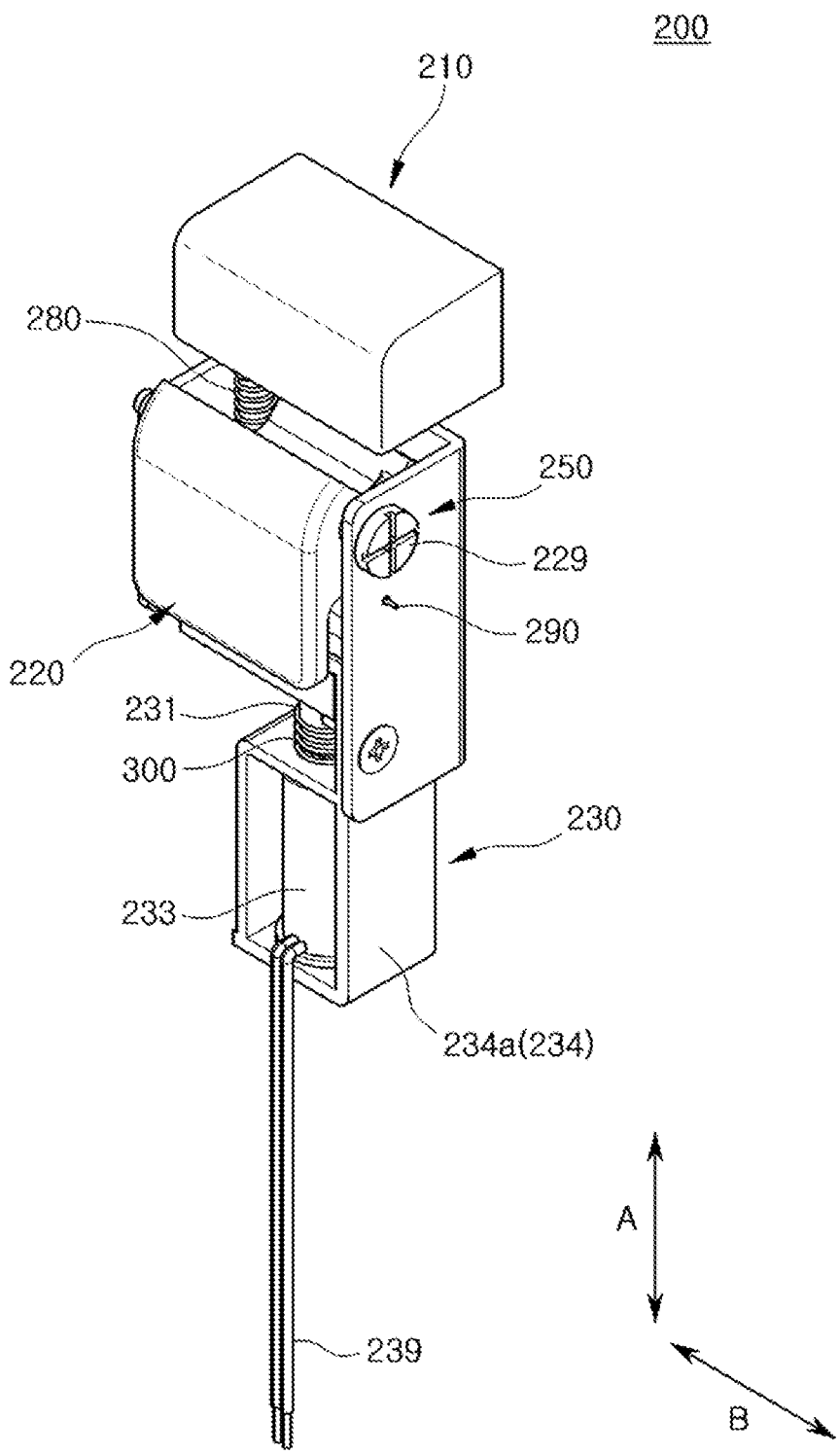
FIG. 4 is a perspective view illustrating the locking unit of the mobile x-ray imaging apparatus according to an embodiment of the present disclosure.
Figure 5:
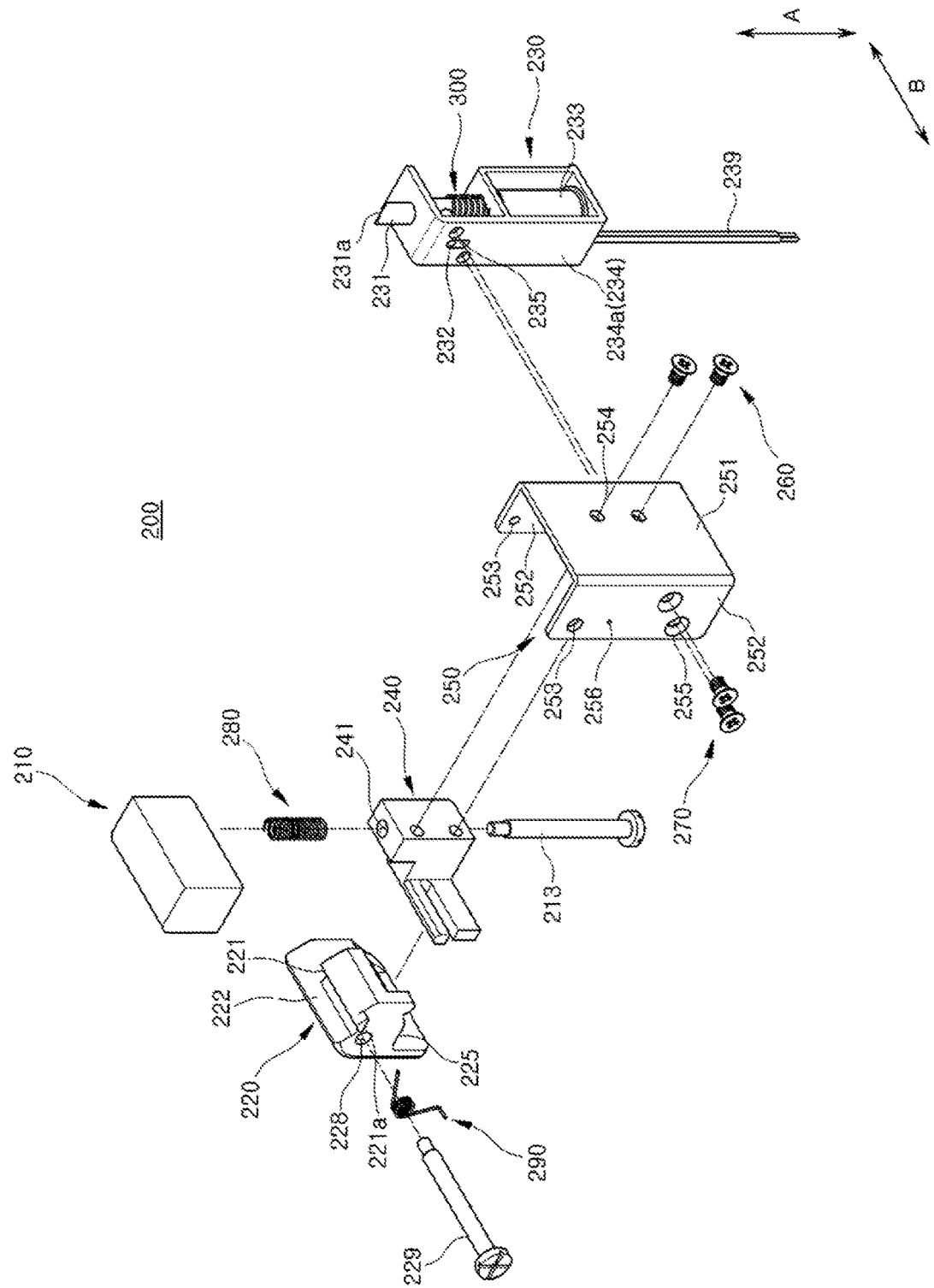
FIG. 5 is an exploded perspective view illustrating the locking unit of the mobile x-ray imaging apparatus according to an embodiment of the present disclosure.

FIG. 4 is a perspective view illustrating the locking unit of the mobile x-ray imaging apparatus according to an embodiment of the present disclosure, and FIG. 5 is an exploded perspective view illustrating the locking unit of the mobile x-ray imaging apparatus according to an embodiment of the present disclosure. Hereinafter, unmarked elements refer to FIGS. 1 to 3.

As illustrated in FIGS. 4 and 5, the one or more locking units 200 may include a pressing member 210. The pressing member 210 may be provided to be pressable. The pressing member 210 may vertically move in a first direction A. In other words, the pressing member 210 may linearly move in the first direction A. The pressing member 210 may move along a guide pin 213. The guide pin 213 may extend in the first direction A to guide movement of the pressing member 210. The guide pin 213 may be coupled to the pressing member 210.

The one or more locking units 200 may further include one or more rotating members 220. A pressing force of the pressing member 210 may be directly transmitted to the one or more rotating members 220. Since elements configured to mechanically connect the pressing member 210 to the one or more rotating members 220 may be omitted when the one or more locking units 200 are designed so that the pressing force of the pressing member 210 may be directly transmitted to the one or more rotating members 220 as described above, miniaturization and structural simplification of the one or more locking units 200 may be realized.

The one or more rotating members 220 may be provided to rotate and protrude toward an inside of the one or more slots 110 and 120. For example, a rotating member 220 of the first locking unit 200a may rotate and protrude toward the inside of the first slot 110. A rotating member 220 of the second locking unit 200b may rotate and protrude toward the inside of the second slot 120. The one or more rotating members 220 may rotate about a rotation shaft 229 configured to extend in a second direction B. The rotation shaft 229 may pass through the one or more rotating members 220 in the second direction B. The first direction A and the second direction B may be perpendicular to each other.

Each of the one or more rotating members 220 may include a pressing portion 221 provided to be pressed by the pressing member 210. Each of the one or more rotating members 220 may further include a rotation limiting portion 222 provided to limit rotation of the one or more rotating members 220. The pressing portion 221 and the rotation limiting portion 222 may have shapes that protrude toward the pressing member 210 in the first direction A. The rotation limiting portion 222 may be provided in front of the pressing portion 221 in a direction R in which the one or more rotating members 220 rotate by being pressed by the pressing member 210. The pressing portion 221 may face a lower surface 211 of the pressing member 210 (see FIG. 6A), and the rotation limiting portion 222 may face a front surface 212 of the pressing member 210 in the direction R in which the one or more rotating members 220 rotate by being pressed by the pressing member 210 (see FIG. 6A).

Each of the one or more rotating members 220 may further include a rod-corresponding surface 225 configured to face a rotation limiting unit 230. Specifically, each of the one or more rotating members 220 may further include the rod-corresponding surface 225 configured to face a rod 231. One end portion of the rod 231 facing the rod-corresponding surface 225 may move along the rod-corresponding surface 225 when the one or more rotating members 220 rotate. A locking groove 227 configured to limit rotation of the one or more rotating members 220 by the one end portion of the rod 231 being inserted thereinto may be formed to be recessed at the rod-corresponding surface 225.

Figure 6A:
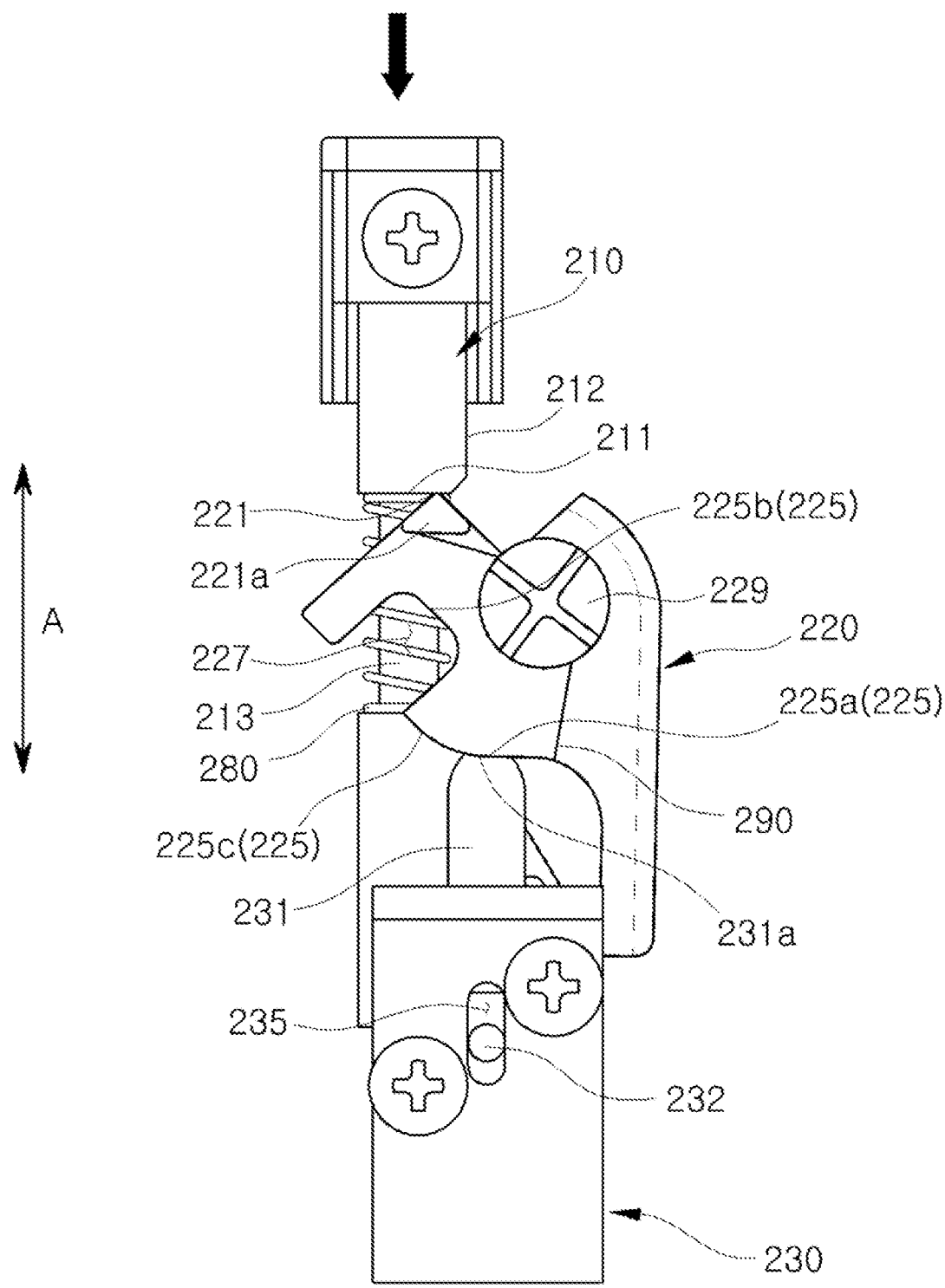
FIGS. 6A to 6C are views illustrating an operational process of the locking unit for locking a slot in the mobile x-ray imaging apparatus according to an embodiment of the present disclosure.

The rod-corresponding surface 225 may include a first portion 225a disposed in front of a second portion 225b in the direction R in which the one or more rotating members 220 rotate by being pressed by the pressing member 210 (see FIG. 6A). Also, the rod-corresponding surface 225 may further include a second portion 225b disposed behind the first portion 225a in the direction R in which the one or more rotating members 220 rotate by being pressed by the pressing member 210 (see FIG. 6A). The second portion 225b may be formed above the first portion 225a in the first direction A. The locking groove 227 may be formed to be recessed at the second portion 225b. Also, the rod-corresponding surface 225 may further include a third portion 225c configured to connect the first portion 225a to the second portion 225b (see FIG. 6A). The third portion 225c may be tilted toward the second portion 225b in the first direction A on the basis of a state in which the one or more slots 110 and 120 are unlocked. A slope may be formed rearward in the direction R in which the one or more rotating members 220 rotate with respect to the first direction A at one surface 231a of the rod 231 facing the rod-corresponding surface 225. Consequently, the rod 231 may smoothly pass through the third portion 225c while the one surface 231a of the rod 231 is in contact with the third portion 225c when the one or more rotating members 220 rotate.

The one or more rotating members 220 may also be integrally formed with the pressing member 210.

The one or more locking units 200 may further include the rotation limiting unit 230 configured to limit the rotation of the one or more rotating members 220. The rotation limiting unit 230 may face the pressing member 210 and the one or more rotating members 220 may be placed therebetween.

The rotation limiting unit 230 may include the rod 231. The rod 231 may vertically move in the first direction A which is the same as a moving direction of the pressing member 210. In other words, the rod 231 may linearly move in the first direction A which is the same as the moving direction of the pressing member 210.

The rotation limiting unit 230 may further include a solenoid 233 coupled to the rod 231 to adjust movement of the rod 231 according to an electrical signal. The solenoid 233 may be connected via a cable 239 to a controller configured to control whether the solenoid 233 is operated. The solenoid 233 may mostly operate during a process in which the one or more slots 110 and 120 are being unlocked. That is, when a user inputs a command for unlocking the one or more slots 110 and 120, the rod 231 moves downward in the first direction A when the solenoid 233 is operated. Accordingly, the one end portion of the rod 231 is detached from the locking groove 227, and the one or more rotating members 220 are restored to a state of before being pressed by the pressing member 210. Consequently, the one or more slots 110 and 120 are unlocked. A user may input a password or use a radiofrequency (RF) card to command the one or more slots 110 and 120 to be unlocked.

The rotation limiting unit 230 may further include a casing 234 configured to have the rod 231 and the solenoid 233 mounted therein. A rod guide 235 may be formed at one sidewall 234a of the casing 234. The rod guide 235 may have a shape that extends in the first direction A to limit movement of the rod 231. A stopper 232 configured to protrude from the rod 231 may be formed at the rod 231. Movement of the rod 231 may be limited by interference between the stopper 232 and the rod guide 235. The stopper 232 formed to protrude from the rod 231 may vertically move in the first direction A and be coupled to the rod guide 235 to limit vertical movement of the rod 231.

The one or more locking units 200 may further include a connecting member 240 configured to connect the pressing member 210 to the rotation limiting unit 230. Specifically, the connecting member 240 may connect the pressing member 210 to the casing 234. A guide pin through-hole 241 through which the guide pin 213 passes may be formed at the connecting member 240. That is, the guide pin 213 may pass through the guide pin through-hole 241 in the first direction A and may be coupled to the pressing member 210.

The one or more locking units 200 may further include a support member 250 installed in the storage unit 100. For example, the support member 250 of the first locking unit 200a may be installed in the partition 130 configured to divide the one or more slots 110 and 120. The support member 250 of the second locking unit 200b may be installed at the frame 140.

The support member 250 may include an installing portion 251 installed in the storage unit 100. Also, the support member 250 may further include a plurality of ribs 252 extending forward in the direction R in which the one or more rotating members 220 rotate by being pressed by the pressing member 210. A rotation shaft coupling hole 253 may be formed at the plurality of ribs 252. The rotation shaft 229 may pass through the support member 250 and the one or more rotating members 220. Specifically, the rotation shaft 229 may pass through the rotation shaft coupling hole 253 of the support member 250 and a rotation shaft through-hole 228 formed at each of the one or more rotating members 220. The connecting member 240 may be fixed and coupled to the support member 250 by a fixing member 260 configured to pass through a fixing hole 254 formed at the installing portion 251. The casing 234 may be fixed and coupled to the support member 250 by an engaging member 270 configured to pass through an engaging hole 255 formed at the plurality of ribs 252 of the support member 250. The fixing member 260 and the engaging member 270 may include, for example, a screw.

The one or more locking units 200 may further include a first elastic member 280. The first elastic member 280 may include a tensile spring configured to be repeatedly contracted and relaxed in the first direction A. The first elastic member 280 may be provided at the guide pin 213 and repeatedly be contracted and relaxed according to movement of the pressing member 210. Specifically, when the pressing member 210 moves downward in the first direction A, the first elastic member 280 may be contracted. Conversely, when the pressing member 210 moves upward in the first direction A, the first elastic member 280 may be relaxed. The pressing member 210 may be restored to a state of before being pressed by a restoration force of the first elastic member 280.

The one or more locking units 200 may further include a second elastic member 290. The second elastic member 290 may include a torsion spring configured to be repeatedly contracted and relaxed according to rotation of the one or more rotating members 220. The second elastic member 290 may be provided at the rotation shaft 229. One end portion of the second elastic member 290 may be fixed to one sidewall of the support member 250. Specifically, the one end portion of the second elastic member 290 may be inserted into a hole 256 formed at the plurality of ribs 252 and fixed. The other end portion of the second elastic member 290 may be fixed to a protrusion 221a formed at each of the one or more rotating members 220 or may be supported by the protrusion 221a. The protrusion 221a may be formed to protrude from the one sidewall of the support member 250 to which the one end portion of the second elastic member 290 is fixed, i.e., one surface of each of the one or more rotating members 220 facing the plurality of ribs 252 of the support member 250 to which the one end portion of the second elastic member 290 is fixed. When described according to another aspect, the protrusion 221a may extend from the pressing portion 221 of each of the one or more rotating members 220 in the second direction B to face the plurality of ribs 252 of the support member 250 to which the one end portion of the second elastic member 290 is fixed. When the one or more rotating members 220 are pressed by the pressing member 210, the second elastic member 290 may be contracted. Conversely, when the one or more rotating members 220 are not pressed by the pressing member 210, the second elastic member 290 may be relaxed. The one or more rotating members 220 may be restored to a state of before being pressed by a restoration force of the second elastic member 290.

The one or more locking units 200 may further include a third elastic member 300. The third elastic member 300 may include a tensile spring configured to be repeatedly contracted and relaxed in the first direction A. The third elastic member 300 may be provided at the rod 231 and be repeatedly contracted and relaxed in the first direction A according to movement of the rod 231. Specifically, when the one end portion of the rod 231 is inserted into the locking groove 227, the third elastic member 300 may be relaxed. Conversely, when the one end portion of the rod 231 is detached from the locking groove 227, the third elastic member 300 may be contracted. When described according to another aspect, the third elastic member 300 may be relaxed when the first elastic member 280 is contracted, and the second elastic member 290 may be contracted when the first elastic member 280 is relaxed.

Figure 6B:
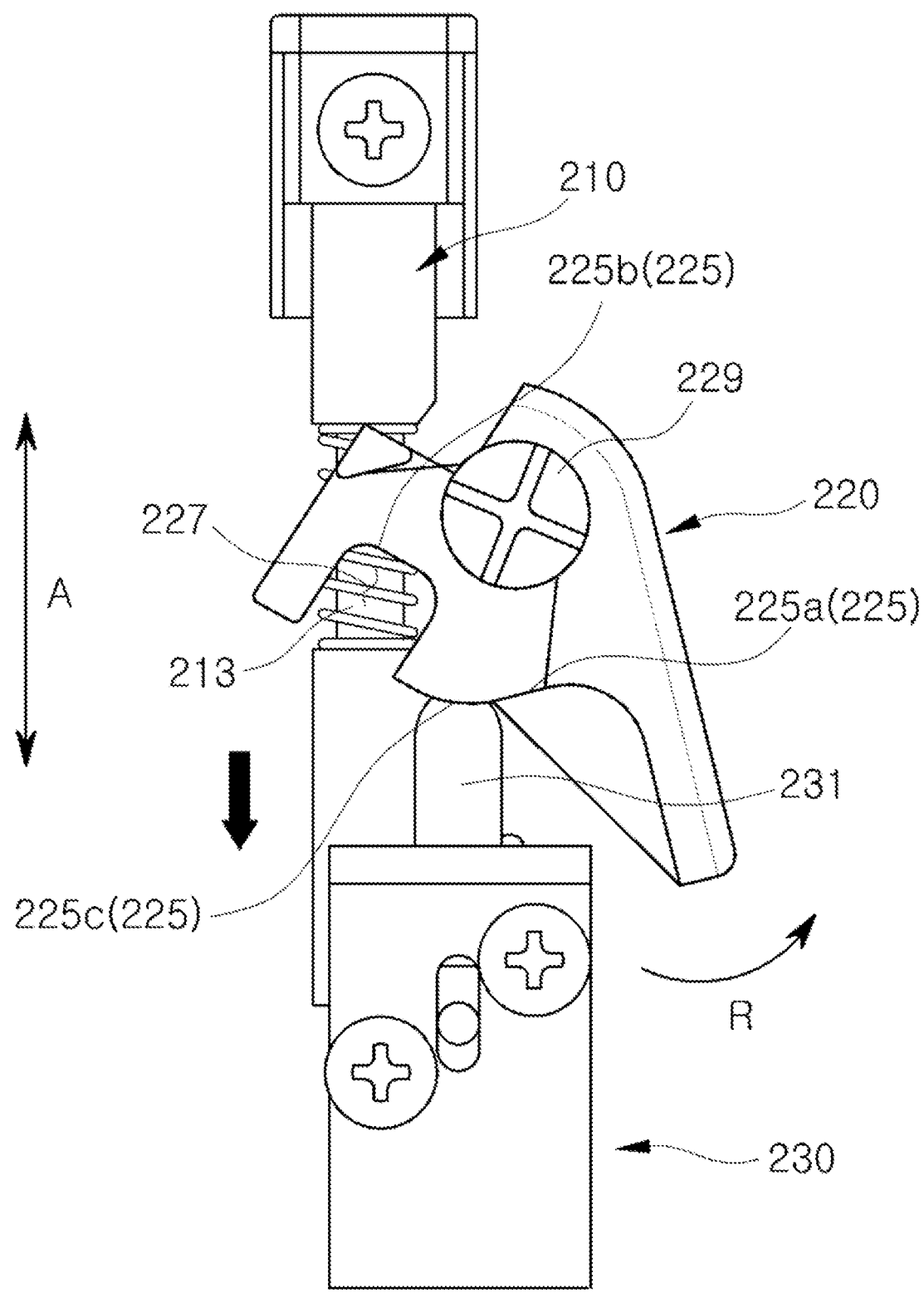
Figure 6C:
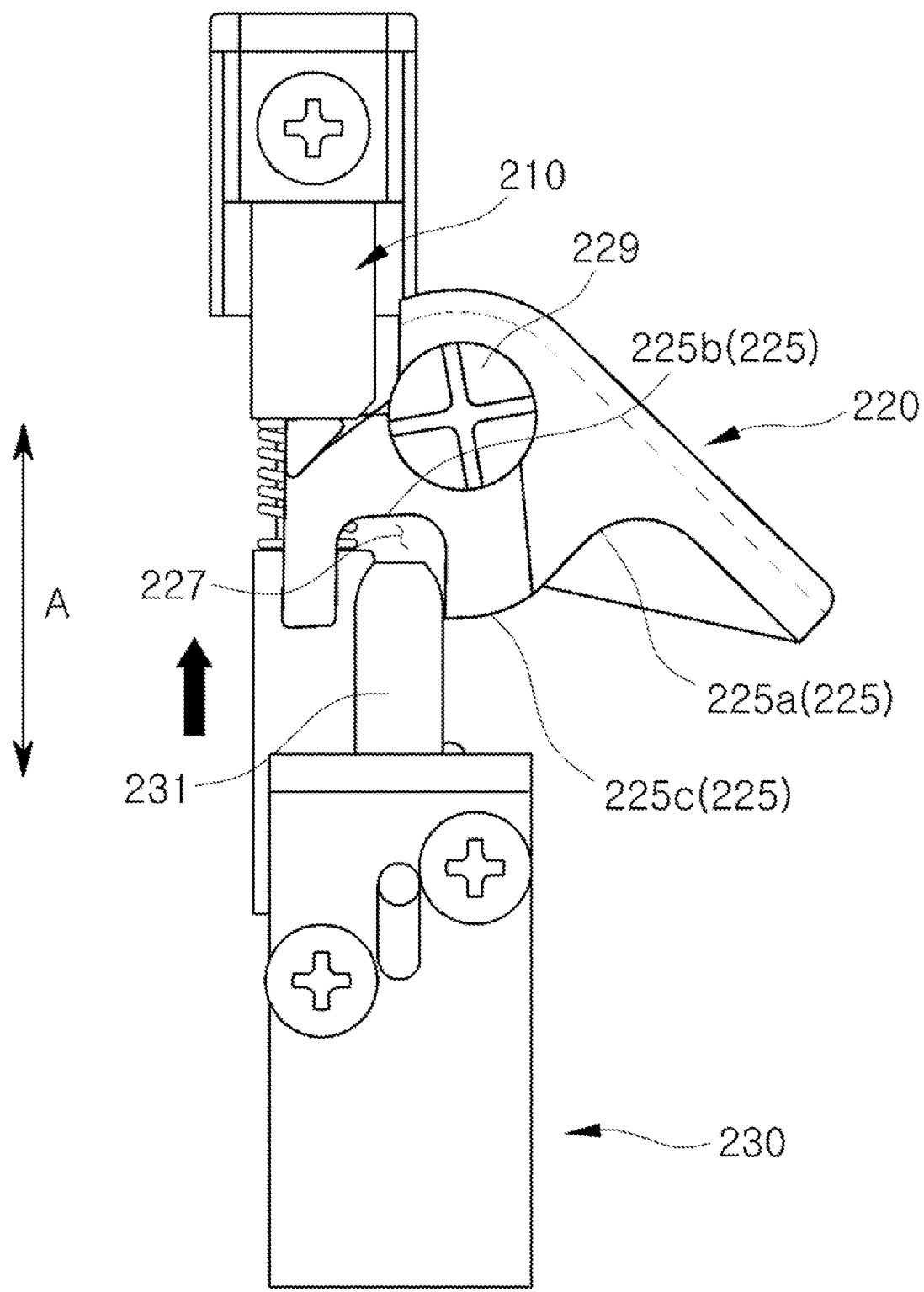

FIGS. 6A to 6C are views illustrating an operational process of the locking unit for locking a slot in the mobile x-ray imaging apparatus according to an embodiment of the present disclosure. Unmarked elements refer to FIGS. 2 to 5.

As illustrated in FIGS. 6A to 6C, when the pressing member 210 is pressed, the pressing force of the pressing member 210 is directly transmitted to the one or more rotating members 220. The one or more rotating members 220 rotate and protrude toward the inside of the one or more slots 110 and 120 by the pressing force. When the one or more rotating members 220 protrude toward the inside of the one or more slots 110 and 120 as described above, withdrawal of the one or more x-ray detectors 30 stored in the one or more slots 110 and 120 may be interfered with and theft of the one or more x-ray detectors 30 may be prevented. The one end portion of the rod 231 facing the rod-corresponding surface 225 moves along the rod-corresponding surface 225 when the one or more rotating members 220 rotate, and rotation of the one or more rotating members 220 is limited when the one end portion of the rod 231 is inserted into the locking groove 227 formed at the one or more rotating members 220. Here, the first elastic member 280 and the second elastic member 290 are contracted and the third elastic member 300 is relaxed. The rod 231 moves upward in the first direction A by a restoration force of the third elastic member 300. The one or more slots 110 and 120 may be locked by the process described above. When the one or more slots 110 and 120 are locked, the rotation shaft 229 may be disposed above the locking groove 227 in the first direction A.

Figure 7A:
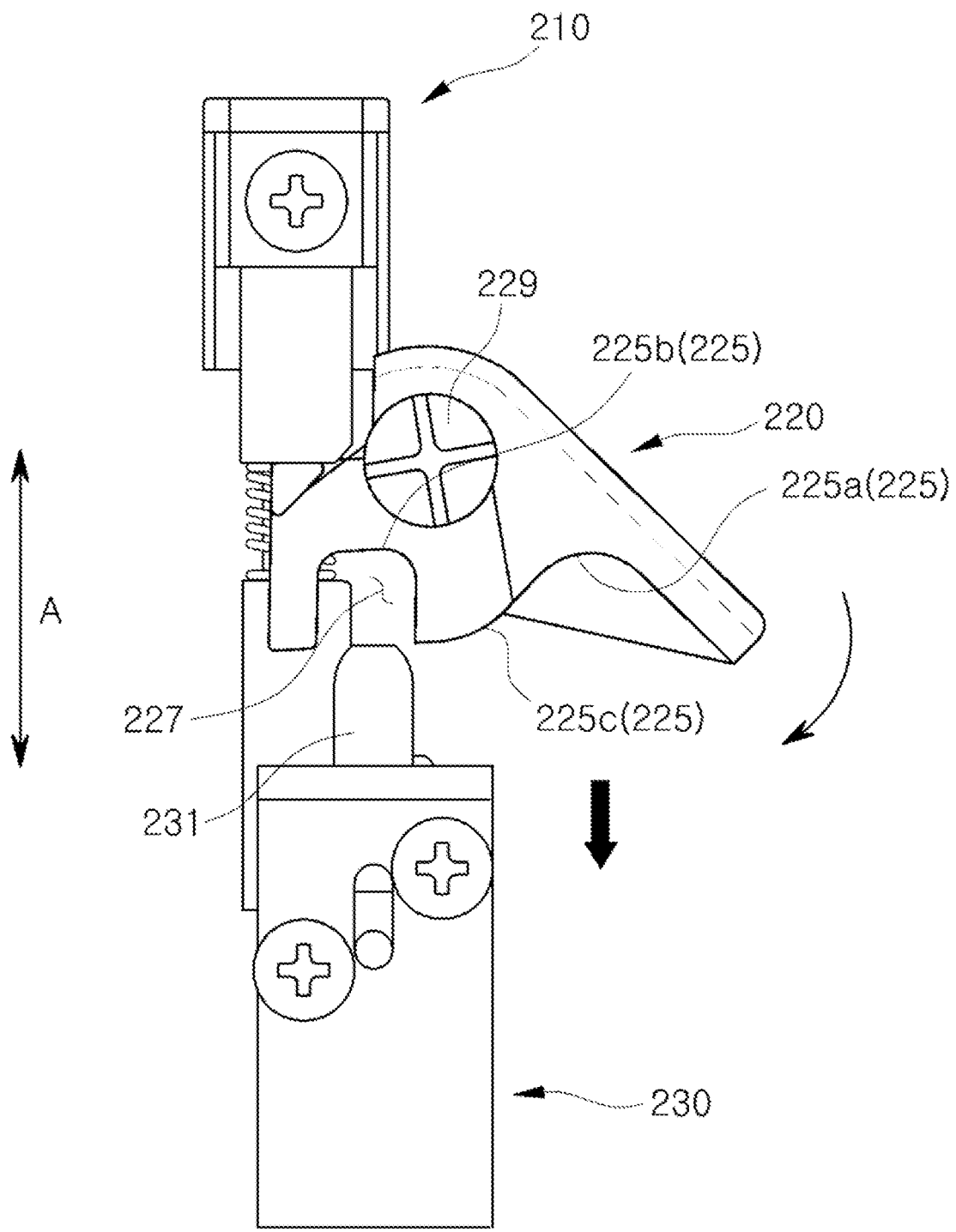
FIGS. 7A and 7B are views illustrating an operational process of the locking unit for unlocking a slot in the mobile x-ray imaging apparatus according to an embodiment of the present disclosure.
Figure 7B:
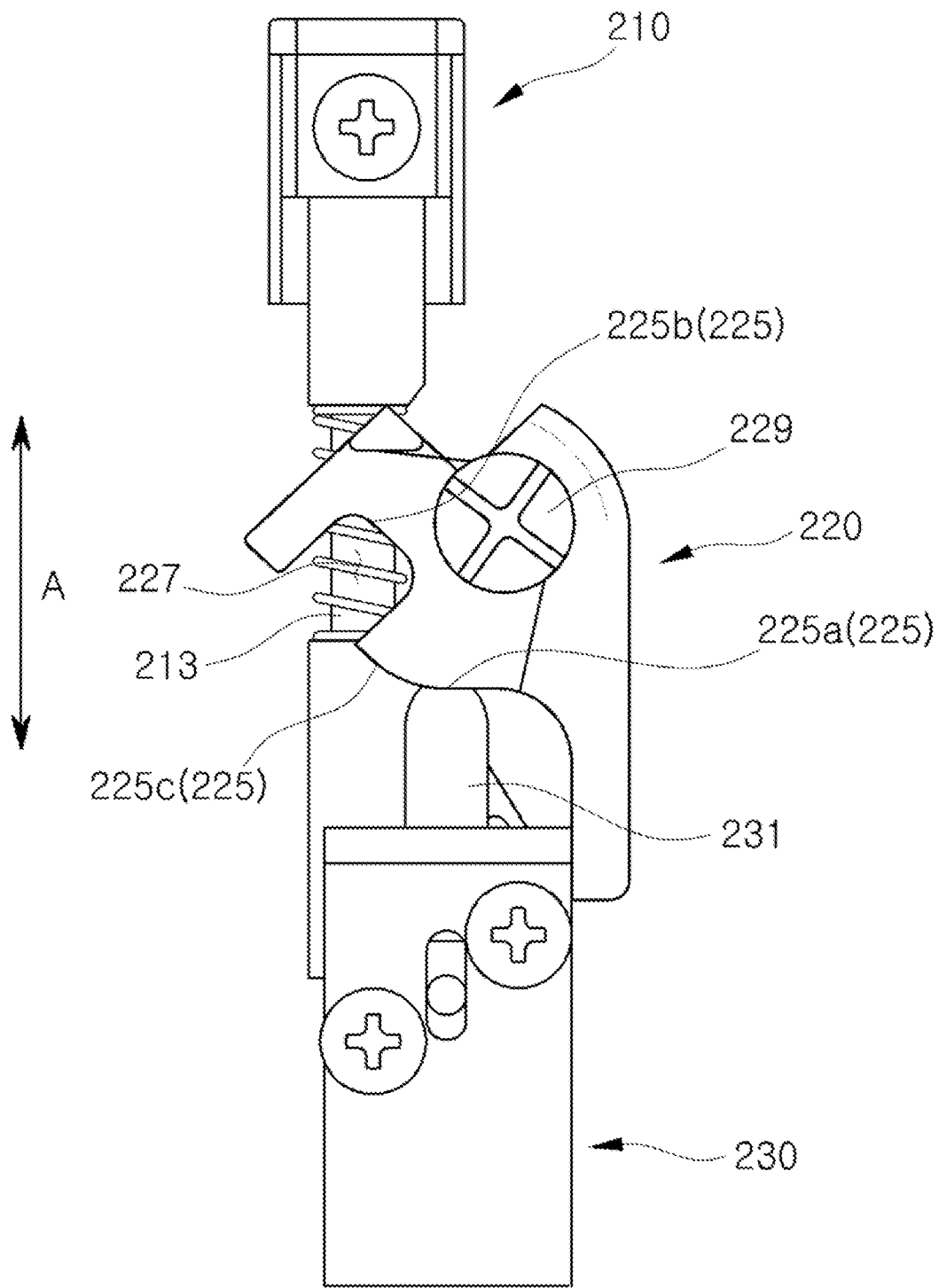

FIGS. 7A and 7B are views illustrating an operational process of the locking unit for unlocking a slot in the mobile x-ray imaging apparatus according to an embodiment of the present disclosure. Unmarked elements should be referred to FIGS. 2 to 5.

As illustrated in FIGS. 7A and 7B, the solenoid 233 is operated when a user inputs a command for unlocking the one or more slots 110 and 120. The rod 231 moves downward in the first direction A by the solenoid 233 being operated. The one end portion of the rod 231 is detached from the locking groove 227 when the rod 231 moves downward in the first direction A, and the one or more rotating members 220 are restored to a state of before being pressed by the pressing member 210 by the restoration force of the second elastic member 290. Here, the first elastic member 280 and the second elastic member 290 are relaxed, and the third elastic member 300 is contracted. The one or more slots 110 and 120 may be unlocked by the process described above.

Figure 8:
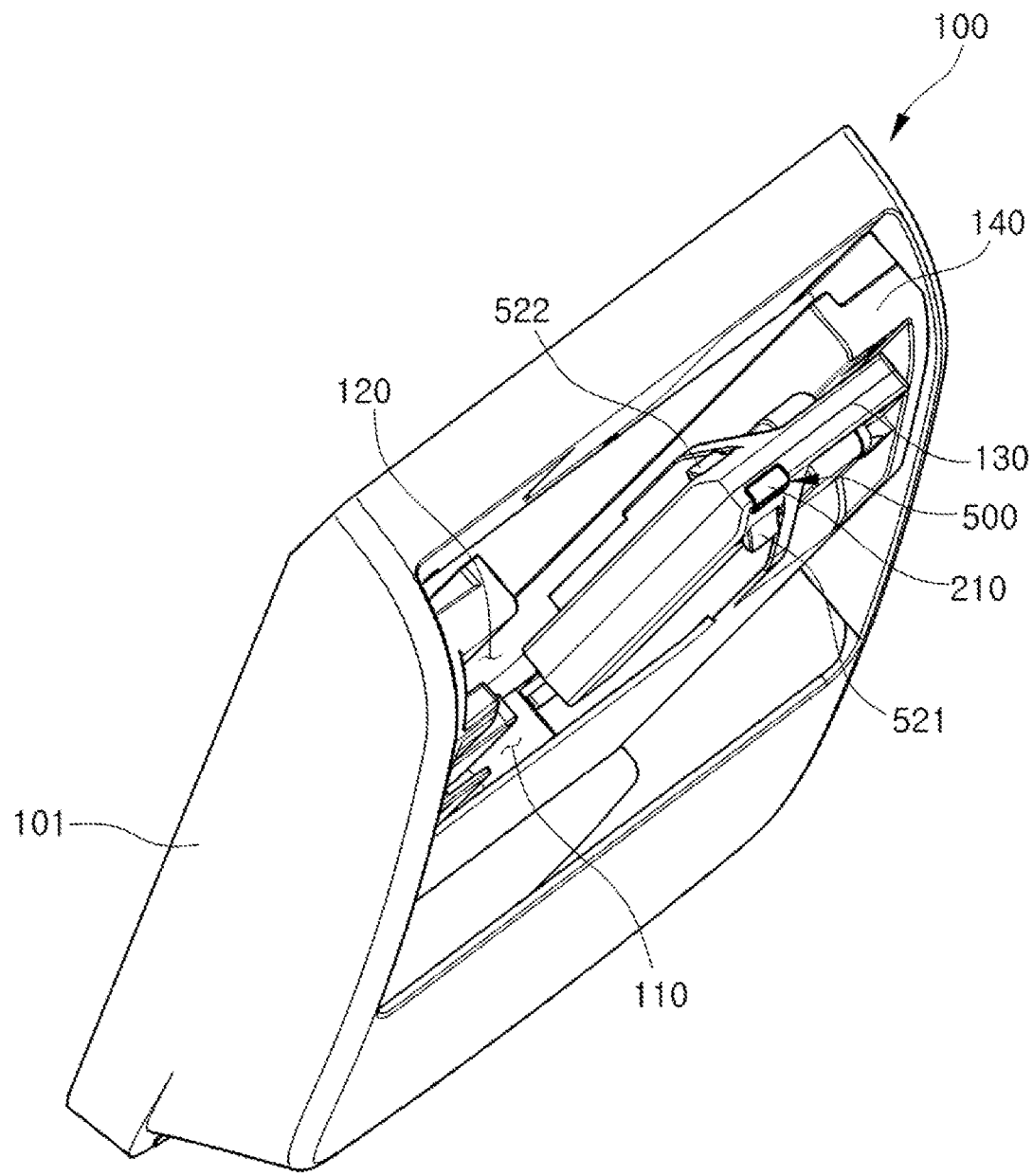
FIG. 8 is a perspective view illustrating a storage unit of the mobile x-ray imaging apparatus according to another embodiment of the present disclosure.

FIG. 8 is a perspective view illustrating a storage unit of a mobile x-ray imaging apparatus according to another embodiment of the present disclosure. Hereinafter, descriptions overlapping those with reference to FIGS. 1 to 7B may be omitted. Also, like reference numerals may be given to elements having the same name as elements described with reference to FIGS. 1 to 7B.

As illustrated in FIG. 8, a locking unit 500 may simultaneously limit withdrawal of a plurality of x-ray detectors 30 stored in a plurality of slots 110 and 120. That is, when the plurality of slots 110 and 120 are assumed to include a first slot 110 and a second slot 120 that abut each other and have a partition 130 placed therebetween, withdrawal of the plurality of x-ray detectors 30 stored in the first slot 110 and the second slot 120 may be simultaneously limited by the single locking unit 500.

The locking unit 500 may be installed in the storage unit 100. Specifically, the locking unit 500 may be installed in the partition 130 to simultaneously limit withdrawal of the plurality of x-ray detectors 30 stored in the first slot 110 and the second slot 120.

Figure 9:
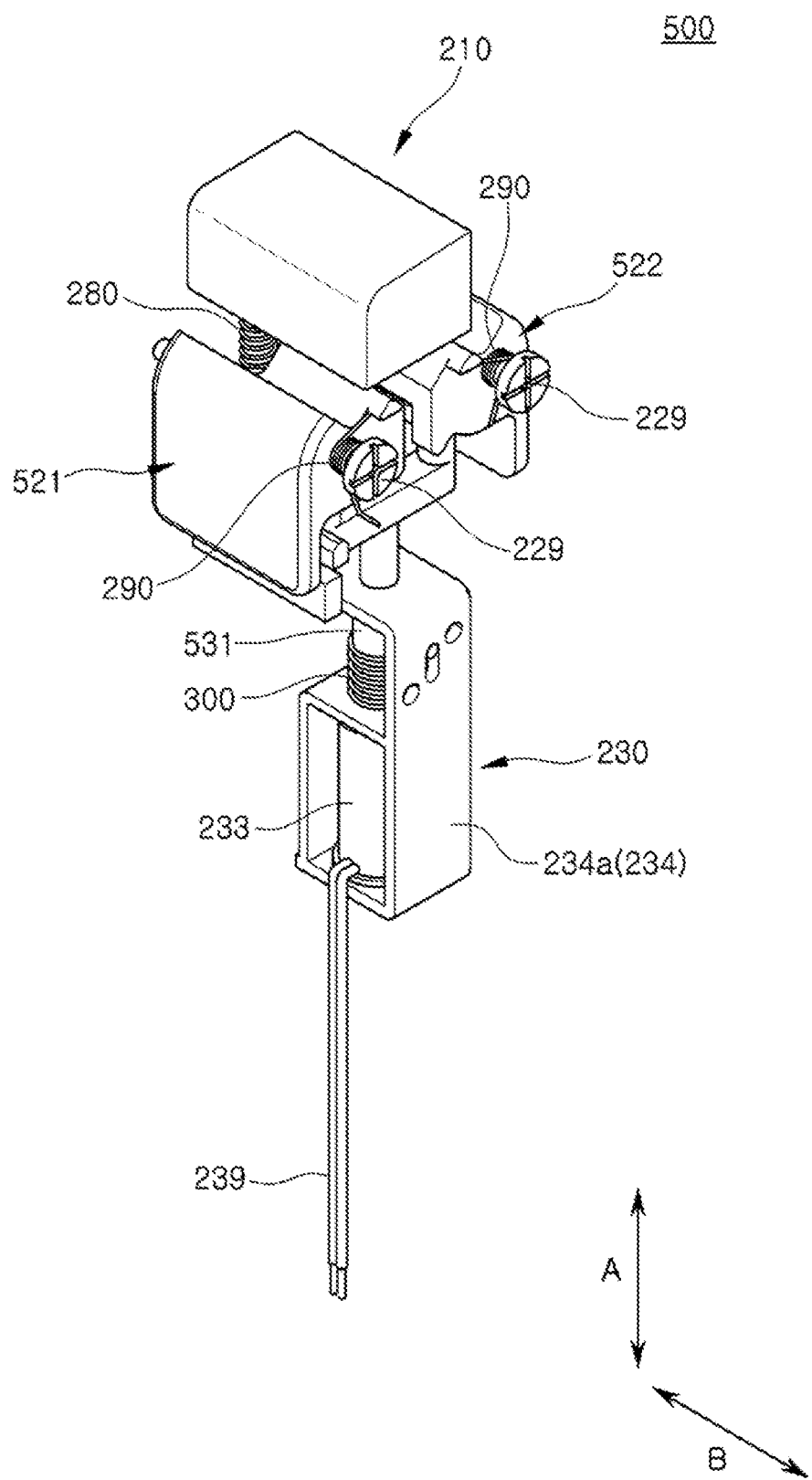
FIG. 9 is a perspective view illustrating a locking unit of the mobile x-ray imaging apparatus according to another embodiment of the present disclosure.
Figure 10:
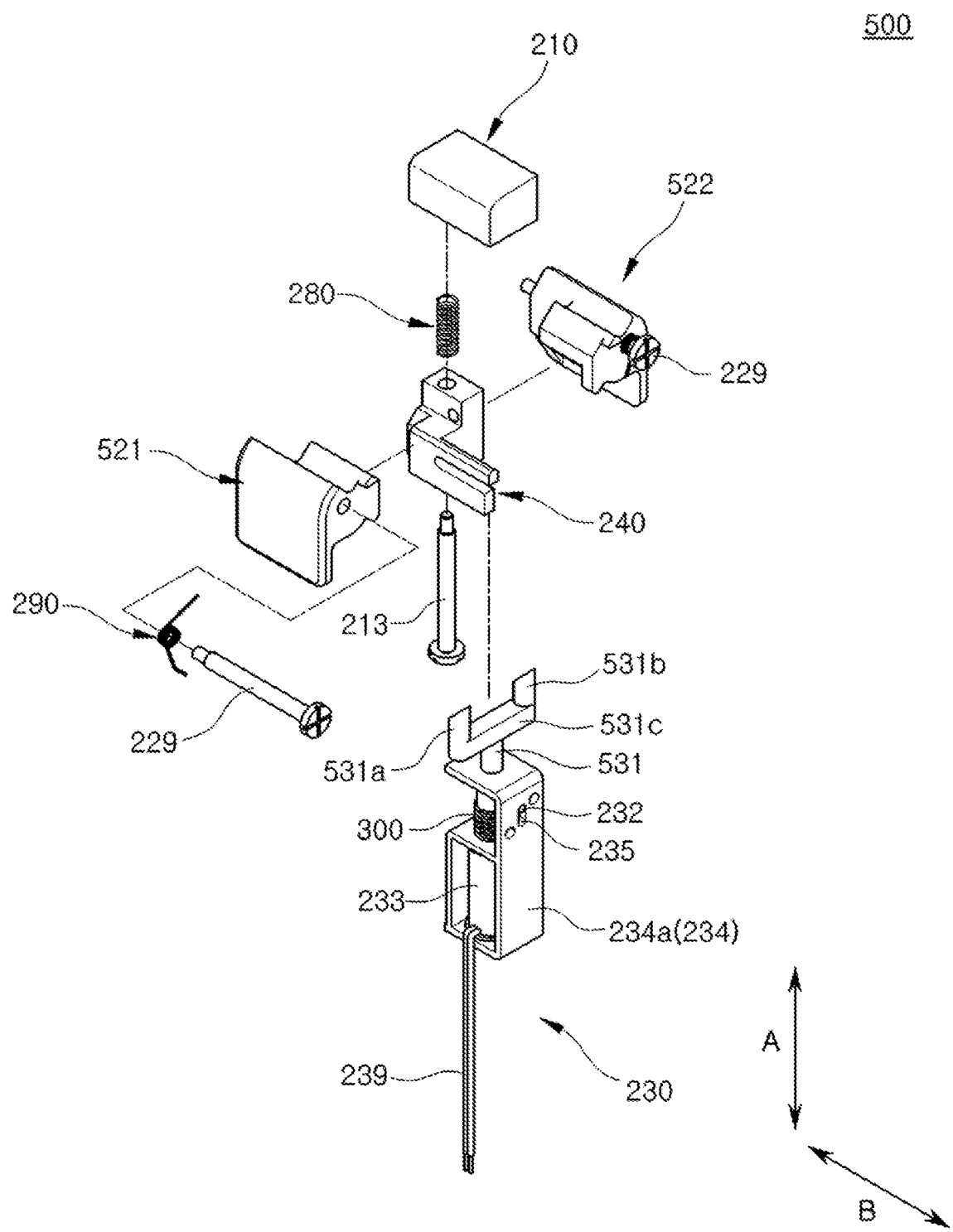
FIG. 10 is an exploded perspective view illustrating the locking unit of the mobile x-ray imaging apparatus according to another embodiment of the present disclosure.

FIG. 9 is a perspective view illustrating a locking unit of the mobile x-ray imaging apparatus according to another embodiment of the present disclosure, and FIG. 10 is an exploded perspective view illustrating the locking unit of the mobile x-ray imaging apparatus according to another embodiment of the present disclosure. Hereinafter, descriptions overlapping those with reference to FIGS. 1 to 7B may be omitted. Also, like reference numerals may be given to elements having the same name as elements described with reference to FIGS. 1 to 7B. A support member 250 is omitted in FIG. 9.

As illustrated in FIGS. 9 and 10, the locking unit 500 may include a pressing member 210 provided to be pressable. The pressing member 210 may be provided to be pressable. The pressing member 210 may vertically move in a first direction A according to a guide pin 213.

The locking unit 500 may further include a plurality of rotating members 521 and 522. The plurality of rotating members 521 and 522 may include a first rotating member 521 provided to rotate and protrude toward an inside of the first slot 110 and a second rotating member 522 provided to rotate and protrude toward an inside of the second slot 120. The pressing member 210 may simultaneously press the plurality of rotating members 521 and 522. Also, a pressing force of the pressing member 210 may be directly transmitted to the plurality of rotating members 521 and 522. The first rotating member 521 and the second rotating member 522 may rotate about rotation shafts 229 extending in the second direction B. The rotation shaft 229 configured to pass through the first rotating member 521 and the rotation shaft 229 configured to pass through the second rotating member 522 may be parallel to each other.

The locking unit 500 may further include a rotation limiting unit 230 configured to simultaneously limit rotation of the plurality of rotating members 521 and 522. The rotation limiting unit 230 may face the pressing member 210 and the plurality of rotating members 521 and 522 may be placed therebetween.

The rotation limiting unit 230 may include a rod 531. The rod 531 may vertically move in the first direction A which is the same as a moving direction of the pressing member 210. The rod 531 may include a first locking portion 531a configured to limit rotation of the first rotating member 521 and a second locking portion 531b configured to limit rotation of the second rotating member 522. Also, the rod 531 may further include a connecting portion 531c configured to connect the first locking portion 531a to the second locking portion 531b so that the first locking portion 531a and the second locking portion 531b may move as one body.

The rotation limiting unit 230 may further include a solenoid 233 coupled to the rod 531 to control movement of the rod 531 according to an electrical signal. The solenoid 233 may be connected via a cable 239 to a controller configured to control whether the solenoid 233 is operated. Because description of the solenoid 233 overlaps description thereof with reference to FIGS. 1 to 7B, the description thereof will be omitted.

The rotation limiting unit 230 may further include a casing 234 in which the rod 531 and the solenoid 233 are mounted. Because description of the casing 234 overlaps description thereof with reference to FIGS. 1 to 7B, the description thereof will be omitted.

As described above, the single pressing member 210 and the single rotation limiting unit 230 may be used to simultaneously control rotation of the plurality of rotating members 521 and 522. In this way, withdrawal of the plurality of x-ray detectors 30 stored in the plurality of slots 110 and 120 may be simultaneously limited.

The plurality of rotating members 521 and 522 may be operated to be symmetrical to each other.

Figure 11:
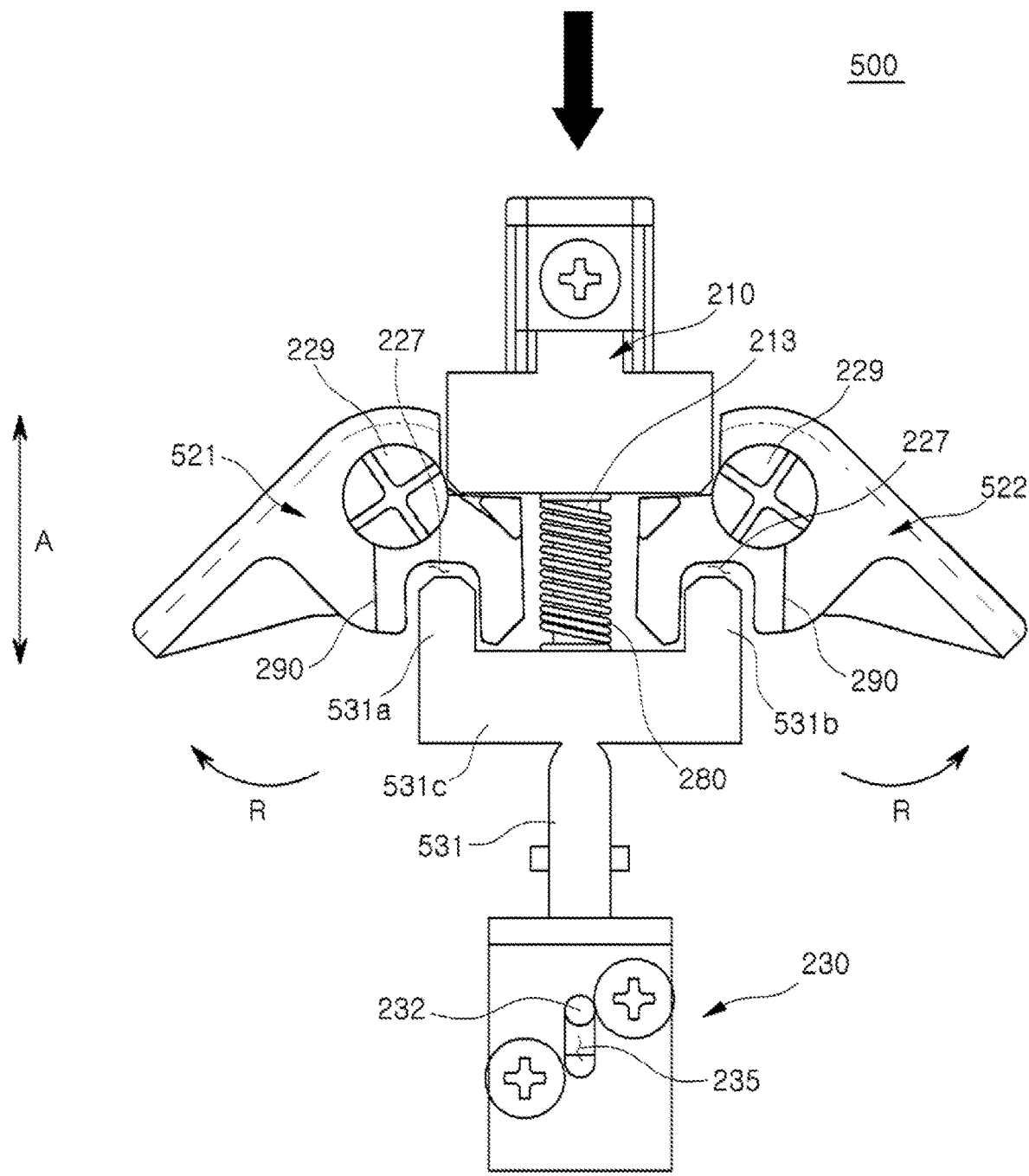
FIG. 11 is a view illustrating the locking unit when a slot in the mobile x-ray imaging apparatus according to another embodiment of the present disclosure is locked.

FIG. 11 is a view illustrating the locking unit when a slot in the mobile x-ray imaging apparatus according to another embodiment of the present disclosure is locked. Hereinafter, descriptions overlapping those with reference to FIGS. 1 to 7B may be omitted. Also, like reference numerals may be given to elements having the same name as elements described with reference to FIGS. 1 to 7B.

As illustrated in FIG. 11, when the pressing member 210 is pressed, the pressing force of the pressing member 210 is simultaneously transmitted to the plurality of rotating members 521 and 522. The plurality of rotating members 521 and 522 rotate and protrude toward the inside of the plurality of slots 110 and 120 by the pressing force of the pressing member 210. The first locking portion 531a and the second locking portion 531b are configured to face a rod-corresponding surface 225 when the plurality of rotating members 521 and 522 rotate and respectively move along the rod-corresponding surface 225 of the first rotating member 521 and the rod-corresponding surface 225 of the second rotating member 522, and rotation of the plurality of rotating members 521 and 522 is simultaneously limited when the first locking portion 531a and the second locking portion 531b are respectively inserted into a locking groove 227 of the first rotating member 521 and a locking groove 227 of the second rotating member 522. Here, the first elastic member 280 and the second elastic member 290 are contracted, and the third elastic member 300 is relaxed. The rod 531 moves upward in the first direction A by the restoration force of the third elastic member 300.

Figure 12:
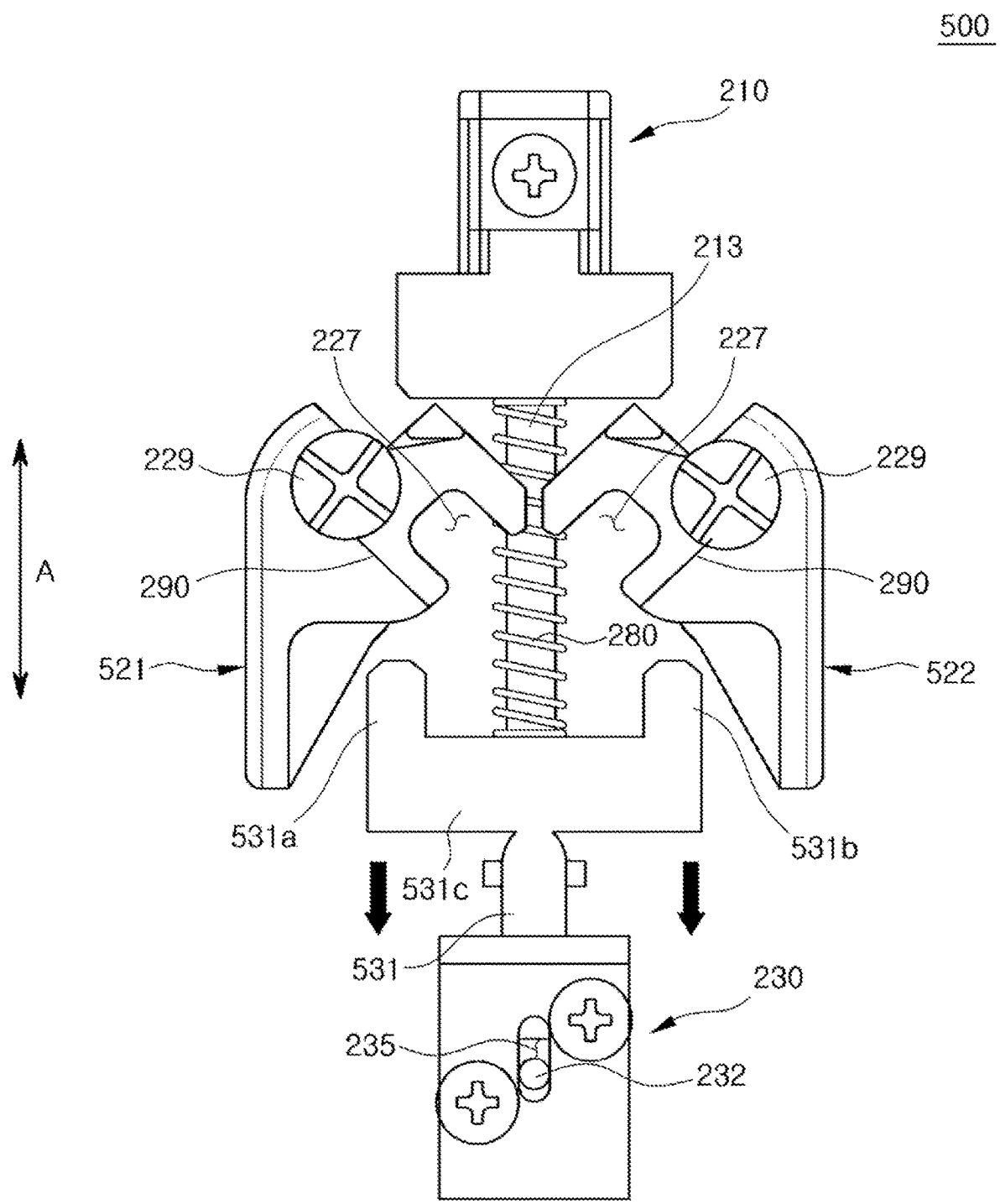
FIG. 12 is a view illustrating the locking unit when a slot in the mobile x-ray imaging apparatus according to another embodiment of the present disclosure is unlocked.

FIG. 12 is a view illustrating the locking unit when a slot in the mobile x-ray imaging apparatus according to another embodiment of the present disclosure is unlocked. Hereinafter, descriptions overlapping those with reference to FIGS. 1 to 7B may be omitted. Also, like reference numerals may be given to elements having the same name as elements described with reference to FIGS. 1 to 7B.

As illustrated in FIG. 12, the solenoid 233 is operated when a user inputs a command for unlocking the plurality of slots 110 and 120. The rod 531 moves downward in the first direction A by the solenoid 233 being operated. The first locking portion 531a and the second locking portion 531b are respectively detached from the locking groove 227 of the first rotating member 521 and the locking groove 227 of the second rotating member 522 when the rod 531 moves downward in the first direction A, and the plurality of rotating member 521 and 522 are restored to a state of before being pressed by the pressing member 210 by the restoration force of the second elastic member 290. Here, the first elastic member 280 and the second elastic member 290 are relaxed, and the third elastic member 300 is contracted.

Although a few exemplary embodiments have been shown and described, it would be appreciated by those skilled in the art that changes may be made in these exemplary embodiments without departing from the principles and spirit of the exemplary embodiments, the scope of which is defined in the claims and their equivalents.

What is claimed is:

1. A method of releasing locking of a slot, the method comprising:
    inserting an X-ray detector into a slot;
    exerting a pressing force on a pressing member in a first direction in which the X-ray detector is inserted into the slot;
    locking the slot as a rotary member receiving the pressing force of the pressing member is rotated in a direction (R) to protrude to an inside of the slot;
    operating a solenoid of a rotation limiting unit when a lock releasing command of the slot is input;
    separating a rod of the rotation limiting unit from a locking groove of the rotary member according to the operation of the solenoid;
    rotating the rotary member in a direction opposite to the direction (R) to prevent the rotary member from protruding to the inside of the slot in response to the rod being separated from the locking groove; and
    withdrawing the X-ray detector from the slot.

2. The method of claim 1, wherein the pressing force of the pressing member is directly transferred to the rotary member.

3. The method of claim 1, wherein inputting the lock releasing command of the slot includes inputting a password of a user or using a radio frequency (RF) card.

4. The method of claim 1, wherein the separating of the rod from the locking groove includes moving the rod downward in the first direction.

5. The method of claim 1, further comprising contracting a third elastic member provided on the rod in the first direction in response to the rod being separated from the lock groove.

6. The method of claim 5, wherein the third elastic member includes a tensile spring that is contracted in the first direction and extended in a direction opposite to the first direction.

7. The method of claim 1, wherein the rotary member rotates about a rotary shaft that extends in a second direction, further comprising:
    rotating the rotary member as a second elastic member on the rotary shaft is extended in response to the rod being separated from the locking groove.

8. The method of claim 7, wherein the second elastic member includes a torsion spring repeating contraction and extension according to a rotation of the rotary member.

9. The method of claim 1, wherein the pressing member moves up and down directions along a guide pin extending in the first direction,
- further comprising extending a first elastic member provided on the guide pin in a direction opposite to the first direction in response to the rod being separated from the locking groove.

10. The method of claim 9, wherein the first elastic member includes a tensile spring that is contracted in the first direction and extended in a direction opposite to the first direction.

11. The method of claim 1, wherein the rotary member includes a rod corresponding surface that faces the rod and has a first portion located on a front side in the direction (R) in which the rotary member is rotated, a second portion located on a rear side in the direction (R) and forming the locking groove, and a third portion connecting the first portion to the second portion,
- an end portion of the rod separated from the locking groove is moved along the third portion of the rod corresponding surface according to rotation of the rotary member, to be disposed on the first portion.

* * * * *